US011596338B2

(12) United States Patent
Futashima et al.

(10) Patent No.: US 11,596,338 B2
(45) Date of Patent: *Mar. 7, 2023

(54) BIOELECTRODE

(71) Applicant: NOK CORPORATION, Tokyo (JP)

(72) Inventors: Ryo Futashima, Fujisawa (JP); Yasushi Sugiyama, Fujisawa (JP); Toru Uda, Fujisawa (JP)

(73) Assignee: NOK CORPORATION ( * ) Notice: Subject to any disclaimer, the term of this patent is extended or adjusted under 35 U.S.C. 154(b) by 206 days.

This patent is subject to a terminal disclaimer.

(21) Appl. No.: 16/877,534

(22) Filed: May 19, 2020

(65) Prior Publication Data
US 2020/0275853 A1 Sep. 3, 2020

Related U.S. Application Data

(63) Continuation of application No. PCT/JP2019/000911, filed on Jan. 15, 2019.

(30) Foreign Application Priority Data

Jan. 15, 2018 (JP) .............................. JP2018-004455

(51) Int. Cl.
A61B 5/25 (2021.01)
H01B 1/22 (2006.01)
C08K 3/08 (2006.01)
C08J 7/044 (2020.01)
C08C 19/00 (2006.01)
C08J 3/20 (2006.01)
C08L 83/04 (2006.01)
C08L 83/12 (2006.01)
C09D 183/04 (2006.01)
C08J 7/14 (2006.01)

(52) U.S. Cl.
CPC ............... *A61B 5/25* (2021.01); *C08C 19/00* (2013.01); *C08J 3/203* (2013.01); *C08J 7/044* (2020.01); *C08J 7/14* (2013.01); *C08K 3/08* (2013.01); *C08L 83/04* (2013.01); *C08L 83/12* (2013.01); *C09D 183/04* (2013.01); *H01B 1/22* (2013.01); *A61B 2562/0215* (2017.08); *C08K 2003/0806* (2013.01); *C08L 2203/20* (2013.01); *C08L 2205/025* (2013.01); *C08L 2312/00* (2013.01)

(58) Field of Classification Search
None
See application file for complete search history.

(56) References Cited

U.S. PATENT DOCUMENTS

| 5,449,714 | A |  | 9/1995 | Inoue et al. |  |
|---|---|---|---|---|---|
| 6,010,646 | A | * | 1/2000 | Schleifstein | C08K 9/02 252/521.5 |
| 10,184,779 | B2 |  | 1/2019 | Norisada et al. |  |
| 2008/0008757 | A1 |  | 1/2008 | Kessell et al. |  |
| 2012/0177934 | A1 |  | 7/2012 | Vogel et al. |  |
| 2017/0145257 | A1 | * | 5/2017 | Osada | G06F 3/041 |
| 2018/0085019 | A1 | * | 3/2018 | Hatakeyama | C09J 11/04 |
| 2018/0116546 | A1 |  | 5/2018 | Pastoor et al. |  |
| 2020/0275850 | A1 | * | 9/2020 | Futashima | A61B 5/25 |
| 2020/0275853 | A1 |  | 9/2020 | Futashima et al. |  |
| 2020/0279669 | A1 | * | 9/2020 | Komori | C08J 7/044 |
| 2020/0305746 | A1 | * | 10/2020 | Futashima | A61B 5/25 |

FOREIGN PATENT DOCUMENTS

| CN | 1889928 A | 1/2007 |
|---|---|---|
| CN | 104293222 A | 1/2015 |
| EP | 3 482 683 A1 | 5/2019 |
| JP | H06-166819 A | 6/1994 |
| JP | 2000-109631 A | 4/2000 |
| JP | 2003-125519 A | 4/2003 |
| JP | 2003-225217 A | 8/2003 |
| JP | 2005-131957 A | 5/2005 |
| JP | 2013-095822 A | 5/2013 |
| JP | 2014-221938 A | 11/2014 |
| JP | 2015-020329 A | 2/2015 |
| JP | 2015-041419 A | 3/2015 |
| JP | 2017128636 A | 7/2017 |
| WO | 2016/189422 A1 | 12/2016 |
| WO | 2018-008688 A1 | 1/2018 |

OTHER PUBLICATIONS

Japanese Office Action for related Application No. JP 2019-564772 dated Mar. 22, 2021 with English translation (4 pages).
Japanese Office Action for corresponding Application No. JP 2019-564773 dated Mar. 22, 2021 with English translation (5 pages).
Japanese Office Action for related Application No. JP 2019-564774 dated Apr. 19, 2021 with English translation (5 pages).
Decision of Refusal for related Japanese Patent Application No. 2019-564774 dated Oct. 18, 2021 with English translation (2 Pages).
Decision of Refusal for related Japanese Application No. 2019-564772 dated Aug. 23, 2021, with English translation (4 pages).
Decision of Refusal for corresponding Japanese Application No. 2019-564773 dated Aug. 23, 2021, with English translation (4 pages).
Extended European Search Report for related Application No. 19738830.9 dated Aug. 13, 2021 (9 pages).

(Continued)

*Primary Examiner* — David J Buttner

(74) *Attorney, Agent, or Firm* — Harness, Dickey & Pierce, P.L.C.

(57) ABSTRACT

A bioelectrode includes a conductive rubber electrode and a silver coating layer provided on the conductive rubber electrode and containing a silicone rubber and silver particles. The silver coating layer contains a modified silicone and contains ions for ion conduction among the silver particles.

2 Claims, 3 Drawing Sheets

(56) References Cited

OTHER PUBLICATIONS

Cranny, A W J, et al., "Thick Film Silver-Silver Chloride Reference Electrodes", Measurement Science and Technology, IPO, Bristol, GB, vol. 9, No. 9, Sep. 1, 1998, pp. 1557-1565, XP020064598.
Extended European Search Report for corresponding Application No. 19738971.1 dated Aug. 13, 2021 (9 pages).
International Search Report for corresponding International Application No. PCT/JP2019/000910 dated Apr. 16, 2019 (4 pages) with English translation.
International Search Report for corresponding International Application No. PCT/JP2019/000911 dated Apr. 16, 2019 (4 pages) with English translation.
International Search Report for corresponding International Application No. PCT/JP2019/000912 dated Apr. 16, 2019 (5 pages), with English translation.
International Preliminary Report on Patentability and Written Opinion for corresponding International Application No. PCT/JP2019/000910 dated Jul. 21, 2020 (11 pages) with English translation.
International Preliminary Report on Patentability and Written Opinion for corresponding International Application No. PCT/JP2019/000911 dated Jul. 21, 2020 (11 pages) with English Translation.
International Preliminary Report on Patentability and Written Opinion for corresponding International Application No. PCT/JP2019/000912 dated Jul. 21, 2020 (12 pages) with English translation.
Takeda, S., "The Latest Trend of Various Bioelectric Signal Measurement Electrodes", Special Edition, The Japanese Journal of Medical Instrumentation, vol. 80, No. 1 (2010) p. 28-p. 37 with English translation.
First Office Action dated Aug. 5, 2022 in the corresponding CN application No. 201980005849.9 with English translation (12 pgs.).
First Office Action dated Aug. 10, 2022 in the relevant CN application No. 20198005789.0 with English translation (12 pgs.).
U.S. Office Action for corresponding U.S. Appl. No. 16/877,529 dated Jun. 6, 2022 (31 Pages).
U.S. Office Action for corresponding U.S. Appl. No. 16/877,563 dated Jun. 3, 2022 (12 Pages).
Decision of Refusal issued in corresponding Chinese Application No. 2019800057890 dated Jan. 5, 2023, with English translation (8 Pages).

\* cited by examiner

BIOELECTRODE

CROSS REFERENCE TO RELATED APPLICATIONS

This is a continuation application of International Patent Application No. PCT/JP2019/000911 filed Jan. 15, 2019, which claims the benefit of Japanese Patent Application No. 2018-004455 filed Jan. 15, 2018, and the full contents of all of which are hereby incorporated by reference in their entirety.

BACKGROUND

Technical Field

The present disclosure relates to a bioelectrode.

Description of the Related Art

Bioelectrode materials made of metal such as sheets of highly conductive metals, for example, gold, silver, platinum, and copper have been conventionally used in bioelectrodes. These bioelectrode materials made of metal have poor adhesion to the skin, and detection of electrical signals from the skin is insufficient. When the materials are used as bioelectrodes, it is necessary to apply a gel, cream, paste, or the like to the skin. Additionally, metals, which are rigid, are not suitable to adhere for a long period.

There also exist bioelectrodes composed of an adhesive material such as a gel (also referred to as gel electrodes) (e.g., see The Japanese journal of medical instrumentation, Vol. 80, No. 1 (2010) P. 28-P. 37). In these bioelectrodes, application of a gel, cream, paste, or the like is not required, but trash and dust are likely to adhere to the adhesive material, and the adherence is gradually lost. For this reason, such bioelectrodes are not suitable for repetitive use. There are also known electrodes obtained by compounding carbon nanotubes in a rubber (e.g., see Japanese Patent Application Publication No. 2015-41419).

Electrodes in which carbon nanotubes and a conductive filler such as a metal powder of Cu, Ag, Au, Al, Ni, and the like are compounded exhibit electrical conductivity by direct contact among conductive filler constituents in the rubber. However, in such electrodes, when external force such as a bend associated with laundry, for example, is applied, contact among filler constituents is removed, and the electrical conductivity decreases (i.e., the strain resistance is poor). For this reason, when long-term use or laundry is conducted, noise is likely to be mixed in measurement signals, and there is further room for improvement in the viewpoint of more suitably measuring intended signals.

SUMMARY

The present disclosure is related to providing a bioelectrode having excellent electrical conductivity and also having excellent strain resistance.

According to an aspect of the present disclosure, a bioelectrode includes a conductive rubber electrode and a silver coating layer provided on the conductive rubber electrode and containing a silicone rubber and silver particles. The silver coating layer contains a modified silicone and contains ions for ion conduction among the silver particles.

In the aspect of the present disclosure, the ions preferably include ions derived from at least one selected from the group consisting of chloride salts, sulfates, and carbonates.

In the aspect of the present disclosure, the modified silicone preferably contains at least one selected from the group consisting of polyether-modified silicones, polyether-alkyl-comodified silicones, polyglycerin-modified silicones, and polyglycerin-alkyl-comodified silicones.

DETAILED DESCRIPTION

Hereinafter, embodiments of the present disclosure will be described with reference to the accompanying drawings. Note that the present disclosure is not limited by the following embodiments in any way.

Figure 1:
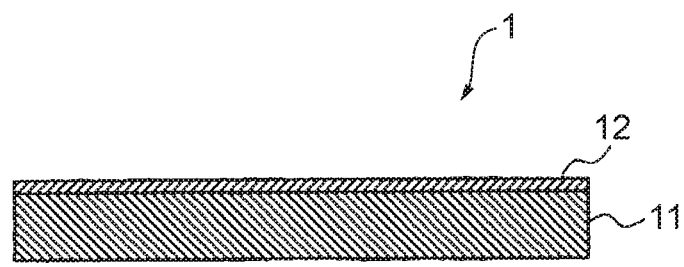
FIG. 1 is a cross-sectional view conceptually illustrating one example of a bioelectrode according to an embodiment of the present disclosure.

FIG. 1 is a cross-sectional view conceptually illustrating one example of a bioelectrode according to the present disclosure. The bioelectrode 1 according to the present embodiment includes a silver coating layer 12 on a conductive rubber electrode 11.

The conductive rubber electrode 11 is obtained by compounding conductive carbon particles in a rubber. The conductive rubber electrode 11 forms a main body of the bioelectrode, and the entire shape of the bioelectrode 1 is imparted by the shape of the conductive rubber electrode 11.

As the rubber constituting the conductive rubber electrode 11, for example, a silicone rubber and the like can be preferably used. The silicone rubber is not especially limited, but organosilicon polymers and the like having a siloxane bond (—Si—O—) as the main chain and having a substituent such as a methyl group, a phenyl group, or a vinyl group or hydrogen as a side chain are preferably used.

The conductive carbon particles are not especially limited as long as the particles can impart electrical conductivity to the silicone rubber mentioned above. As the conductive carbon particles, for example, carbon black, graphite, and the like are preferable. As carbon black, Ketjen black, acetylene black, and the like can be preferably used. Above all, Ketjen black and the like, which have relatively high electrical conductivity, are particularly preferable.

The average particle size of the conductive carbon particles is not especially limited, but is preferably in the range of 0.1 μm or more and 100 μm or less, more preferably in the range of 1 μm or more and 30 μm or less. The average particle size is an average diameter determined by measurement of an electron micrograph and calculation using arithmetic mean.

The amount of the conductive carbon particles to be compounded in the conductive rubber electrode 1 is not especially limited. The amount can be appropriately set in the range where electrical conductivity can be imparted, and is preferably in the range of 10% by mass or more and 70% by mass or less, more preferably in the range of 20% by mass or more and 50% by mass or less.

The silver coating layer 12 is obtained by compounding silver particles to a silicone rubber. The silicone rubber is not especially limited, but preferably used are organosilicon polymers and the like having a siloxane bond (—Si—O—) as the main chain and having a group such as a methyl group, a phenyl group, or a vinyl group or hydrogen as a side chain.

When the silver coating layer 12 is constituted with a silicone rubber, the silicone rubber serves as a binder for the silver particles. Especially, the silver coating layer 12 is retained on the conductive rubber electrode 1 formed of the silicone rubber with a high adhesion, and thus it is possible to prevent the layer from coming off from the electrode. This adhesion also contributes to stabilization of electrical connection between the silver coating layer 12 and the conductive rubber electrode 11. Additionally, a silicone rubber has excellent flexibility, and thus, conformability to movements of a living body is suitably exhibited during use of the bioelectrode. As a result of these, it is possible to suitably reduce the contact impedance with a living body.

In the present embodiment, the silver coating layer 12 contains a modified silicone as an electrical conductivity improving material and includes ions for ion conduction present among the silver particles.

As a result of this, the silver coating layer 12, first, as an electrical conduction mechanism, has electron conductivity derived from the silver particles and ion conductivity derived from ions present among the silver particles. Herein, "electron conduction (conductivity)" means that electrons singly (not as ions) migrate to thereby exhibit electrical conductivity, and "ion conduction (conductivity)" means that ions migrate to thereby exhibit electrical conductivity.

In other words, the silver particles form a network of the conductive particles (silver particles) in the silver coating layer 12 by means of their electron conductivity. Furthermore, causing ions to exist among the silver particles allows the ions to migrate in the silver coating layer 12 to thereby exhibit ion conductivity. Thereby, the electrical conductivity among the silver particles is complemented by the ion conductivity.

Meanwhile, the modified silicone functions as an electrical conductivity improving material that suitably forms a path for migration of the ions in the silver coating layer 12 to thereby facilitate ion conduction.

As a result, in addition to an electrical conduction mechanism by means of electron conduction formed of the network of the conductive particles, an electrical conduction mechanism by means of ion conduction formed by migration of ions is satisfactorily formed. Electron conductivity and ion conductivity synergistically act to reduce the surface resistance and lead to excellent electrical conductivity. Additionally, even in the case where external force such as bending is applied to completely cut the network of the conductive particles, ion conduction complements electrical conduction among conductive particles to suppress an increase in the resistance. For this reason, if the bioelectrode is repetitively deformed, a property with which the electrical conductivity is satisfactorily maintained (strain resistance) is improved.

As the modified silicone as an electrical conductivity improving material, ones obtained by introducing a side chain that causes modification in the main chain formed of a siloxane bond (—Si—O—; also referred to as a silicone chain) can be preferable used. Examples thereof include silicones containing polyether modification, polyether-alkyl comodification, polyglycerin modification, polyglycerin-alkyl comodification, or the like. The side chain that causes modification preferably contains an ether bond (—C—O—C—).

As the polyether-modified silicone, ones obtained by introducing a side chain formed of a polyether chain into the main chain formed of a silicone chain can be used.

As the polyether-alkyl-comodified silicone, ones obtained by introducing a side chain formed of a polyether chain and a side chain formed of an alkyl chain to the main chain formed of a silicone chain can be used.

As the polyglycerin-modified silicone, ones obtained by introducing a side chain formed of a polyglycerin chain into the main chain formed of a silicone chain can be used.

As the polyglycerin-alkyl-comodified silicone, ones obtained by introducing a side chain formed of a polyglycerin chain and a side chain formed of an alkyl chain into the main chain formed of a silicone chain can be used.

Among these, the polyether-modified silicone or polyglycerin-modified silicone is particularly preferable.

The modified silicone preferably has a viscosity of 100 to 5000 mm$^2$/s and an HLB of about 1 to 15. One of the modified silicones may be used singly or a plurality of the modified silicones may be used in combination.

Figure 2:
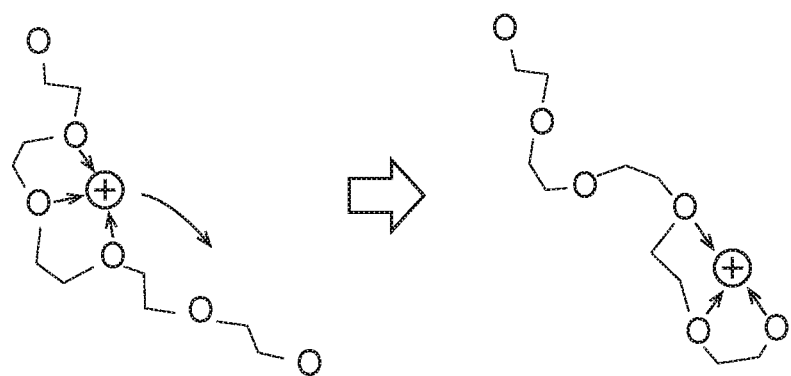
FIG. 2 is a view conceptually illustrating one example of ion conduction facilitation by an electrical conductivity improving material (modified silicone).

FIG. 2 is a view conceptually illustrating one example of ion conduction facilitation by an electrical conductivity improving material (modified silicone), depicting how an introduced side chain (modifying group) coordinates to an ion (here, a cation denoted by (+) in the figure) to stabilize the dissociation state of the ion as well as to form a path through which the ion migrates. The ion can migrate along a side chain or from a side chain to another side chain, and thus, ion conduction is facilitated. The side chain preferably can coordinate to an ion, and here, a side chain having a polyether structure is exemplified.

The amount of the modified silicone to be added in the silver coating layer 12 is not especially limited, can be appropriately set in the range where the silicone rubber can be cured, and is preferably 2 parts by mass or more and 100 parts by mass or less.

The silver particles are not especially limited as long as the silver particles are dispersible in the silicone rubber. At least one type of aggregated silver powders and flaky silver powders can be used. An aggregated silver powder and a flaky silver powder may be mixed and used, or either one type of them may be used.

The aggregated silver powder refers to a silver powder of a plurality of particulate primary particles three-dimensionally aggregated, and an example thereof can be trade name: "G-35" (manufactured by DOWA Electronics Materials Co., Ltd.).

The flaky silver powder refers to a silver powder having a scale-like shape, and examples thereof can include trade name: "327077" (manufactured by Sigma-Aldrich Co. LLC.) and trade name: "FA-D-3" (manufactured by DOWA Electronics Materials Co., Ltd.).

The average particle size of the silver particles is not especially limited, but is preferably in the range of 4 μm or more and 8 μm or less in the case of aggregated ones and preferably in the range of 5 μm or more and 15 μm or less in the case of flaky ones. The average particle size is an average diameter determined by measurement of an electron micrograph and calculation using arithmetic mean.

The total amount of the silver particles to be compounded in the silver coating layer 12 can be appropriately set in the range where electrical conductivity can be imparted, but is preferably in the range of 50 parts by mass or more and 600 parts by mass or less, more preferably in the range of 100 parts by mass or more and 400 parts by mass or less, based on 100 parts by mass of the silicone rubber.

The film thickness of the silver coating layer 12 is not especially limited and is preferably in the range of 10 μm or more and 300 μm or less, more preferably in the range of 15 μm or more and 100 μm or less. This can further enhance adhesion of the silver coating layer 12 with respect to the conductive rubber electrode 11, further prevent delamination of the silver coating layer 12, and additionally lower the contact impedance.

In the case where the conductive rubber electrode 1 mentioned above is in the form of sheet, the film thickness of the silver coating layer 12 can be made smaller than the film thickness of the conductive rubber electrode 1.

In the silver coating layer 12, the type of ions caused to be present among the silver particles is not especially limited, but from the viewpoint of imparting satisfactory ion conductivity, ions derived from a salt such as an inorganic salt (ions obtained by electric dissociation of a salt) are preferable.

Examples of the inorganic salt include chloride salts, sulfates, and carbonates.

Examples of the chloride salt include sodium chloride, potassium chloride, lithium chloride, calcium chloride, and magnesium chloride.

Examples of the sulfate include sodium sulfate, potassium sulfate, lithium sulfate, calcium sulfate, and magnesium sulfate.

Examples of the carbonate include sodium carbonate, potassium carbonate, lithium carbonate, calcium carbonate, and magnesium carbonate.

Among these, from the viewpoint of ion mobility or the viewpoint of solubility in a liquid such as water used for the salt water treatment mentioned below and the like, preferable are chloride salts of an alkali metal such as sodium chloride, potassium chloride, and lithium chloride.

Figure 3:
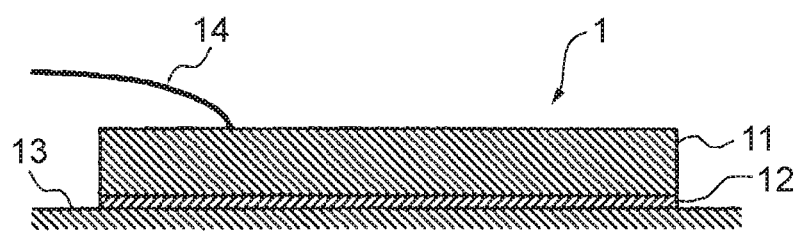
FIG. 3 is a view conceptually illustrating a usage example of the bioelectrode according to the embodiment of the present disclosure.

For example, as shown in FIG. 3, by use of the bioelectrode 1 according to the present embodiment, the conductive rubber electrode 11 is connected to a measuring apparatus via a signal transmission member 14 such as wiring, the surface of the silver coating layer 12 is caused to contact a living body 13, and electrical signals from the living body 13 can be measured in the measuring apparatus.

The bioelectrode 1 according to the present embodiment is preferably used for measuring an electrocardiogram as electrical signals. The bioelectrode 1 according to the present embodiment can be suitably used in medical measuring apparatuses, wearable measuring apparatuses, and health monitoring devices, for example.

In one example of a method for producing the bioelectrode 1 according to the present embodiment, first, a conductive rubber electrode 11 is provided, and a silver coating layer 12 is formed on the conductive rubber electrode 11.

On forming the silver coating layer 12, first, silver particles and a modified silicone, which is a dispersant for the silver particles, are mixed to an uncured liquid silicone rubber (binder), and the mixture is stirred to prepare a silver paste. Meanwhile, it is possible to appropriately compound a crosslinking agent for crosslinking (curing) the silicone rubber to the silver paste. Thereafter, the silver paste prepared is applied on the conductive rubber electrode. Curing the silver paste applied by heating causes the silver coating layer 12 to be formed.

Meanwhile, a method for causing ions of an inorganic salt to exist in the silver coating layer is not especially limited, but, for example, it is possible to use a method including mixing an inorganic salt in an uncured paste for forming the silver coating layer.

An inorganic salt has a low solubility in the paste and is unlikely to be ionized in the paste. Usually, even when such an inorganic salt is mixed in the paste, it is difficult to cause the inorganic salt to exist as ions in the silver coating layer to be obtained. In contrast to this, as long as the modified silicone is contained in the paste, dissociation of the inorganic salt to ions is facilitated by the polarity of the modified silicone and the like, and thus, it is possible to cause the inorganic salt to exist as ions in the silver coating layer to be obtained.

Alternatively, instead of adding the inorganic salt directly to the paste, it is also possible to, for example, dissolve (ionize) the inorganic salt in a solvent such as water to prepare a solution and add this solution to the paste. In the method of adding the solution to the paste, there is a limit on the solubility (compatibility) between the solvent such as water and the paste. In the case where the compatibility is low, the aqueous solution and the paste separate, and the inorganic salt is likely to be unevenly distributed in the silver coating layer 12 to be obtained. Then, the following method can be further preferably used.

In other words, as a further preferable method of causing the ions of the inorganic salt to exist in the silver coating layer 12, it is possible to use a method of immersing a silver coating layer 12 (to which no inorganic salt has not been added yet) formed by drying and curing the paste in a solution of an inorganic salt (also referred to as a salt water treatment). This causes the ions of the inorganic salt dissociated in the solution to penetrate the silver coating layer 12 to thereby enable the ions of the inorganic salt to suitably exist in the silver coating layer 12.

Particularly, molecular chains of a silicone rubber have high mobility, and thus gas or liquid molecules penetrate in the molecular chains more easily, by dissolution or diffusion, than in resins, which are also polymers. It is possible to cause the ions in the inorganic salt in the solution to penetrate from the surface of the silver coating layer by use of this property. This penetration behavior is further facilitated by the combination of the silicone rubber and the modified silicone.

The solvent for use in the solution may be any solvent as long as the solvent can dissolve the inorganic salt, and examples thereof include water, ketones such as acetone and alcohols such as ethanol. Among these, in respect of safety and costs, water, ethanol, or a mixture of water and ethanol is preferable, and water is most preferable.

As described above, an effect of reducing the surface resistance and enhancing the strain resistance of the bioelectrode 1 can be provided by causing the silver coating layer 12 having electron conductivity and ion conductivity in combination to contain an electrical conductivity improving material formed of a modified silicone. This improves the accuracy of the bioelectrode 1 to measure bioelectric signals. For example, even when external force such as bend associated with laundry is applied to remove contact among silver particles, the ion conductivity is maintained to thereby allow the electrical conductivity to be maintained. Additionally, the bioelectrode, which is derived from a silicone rubber or a modified silicone, has excellent flexibility. Thus, even when fitted for a long period, the bioelectrode causes no discomfort and can suitably conform to movements of a living body while maintaining satisfactory electrical conductivity.

In the description hereinabove, the case where the bioelectrode 1 is in the form of sheet has been principally described. However, the shape of the bioelectrode is not limited thereto, and the bioelectrode can have various shapes. Meanwhile, the electrode surface part to be contacted with a living body can be constituted by the silver coating layer 12 mentioned above.

EXAMPLES

Hereinafter, the present disclosure will be described more in detail based on examples conducted to clarify the effects of the present disclosure. Note that the present disclosure is not limited by the following examples and comparative examples in any way.

1. Production of Bioelectrode

Example 1

(1) Production of Conductive Rubber Electrode

To 100 parts by mass of a conductive silicone rubber (trade name: "KE-3801M-U"; containing carbon black, manufactured by Shin-Etsu Chemical Co., Ltd.), 1.0 parts by mass of a crosslinking agent (trade name: "C-8A"; 2,5-dimethyl-2,5-bis(t-butylperoxy)hexane content: 80% by mass, manufactured by Shin-Etsu Chemical Co., Ltd.) was compounded.

Thereafter, a material obtained by kneading the components compounded described above in a kneader for 10 minutes and then further kneading the components with a roll for three minutes, (carbon black content: 6% by volume) was press-crosslinked (primary-crosslinked) at 180° C. for four minutes and thereafter secondary-crosslinked at 230° C. for five hours to provide a conductive rubber electrode having a thickness of 1 mm.

(2) Formation of Silver Coating Layer

To 100 parts by mass of a liquid silicone rubber (trade name: "KE-106", manufactured by Shin-Etsu Chemical Co., Ltd.) as a binder, 150 parts by mass of each of two types of silver particles (trade name: "FA-D-3" and trade name: "G-35"; both manufactured by DOWA Electronics Materials Co., Ltd.) (total amount to be compounded: 300 parts by mass), additionally, as electrical conductivity improving materials, 10 parts by mass of a polyether-modified silicone (trade name: "KF-6015", manufactured by Shin-Etsu Chemical Co., Ltd.) and 10 parts by mass of a polyglycerin-modified silicone (trade name: "KF-6106", manufactured by Shin-Etsu Chemical Co., Ltd.) were mixed, and the mixture was stirred to prepare a silver paste.

Thereafter, the silver paste prepared was applied by screen printing on the conductive rubber electrode obtained in the above-described "(1) Production of Conductive Rubber Electrode" and cured in an oven set at 150° C. for 30 minutes to thereby form a silver coating layer having a film thickness of 54 μm.

Thereafter, as a salt water treatment, the silver coating layer was immersed in a sodium chloride aqueous solution having a concentration of 1% for an hour and then dried. As mentioned above, a bioelectrode was produced.

Example 2

A bioelectrode was produced in the same manner as in Example 1 except that 20 parts by mass of a polyether-modified silicone (trade name: "KF-6015", manufactured by Shin-Etsu Chemical Co., Ltd.) was singly used as the modified silicone.

Example 3

A bioelectrode was produced in the same manner as in Example 1 except that 20 parts by mass of the polyglycerin-modified silicone (trade name: "KF-6106", manufactured by Shin-Etsu Chemical Co., Ltd.) was singly used as the modified silicone.

Comparative Example 1

A bioelectrode was produced in the same manner as in Example 1 except that compounding of the electrical conductivity improving material (modified silicone) was omitted, the film thickness of the silver coating layer was set to 62 μm, and the salt water treatment was omitted.

Comparative Example 2

A bioelectrode was produced in the same manner as in Example 1 except that compounding of the electrical conductivity improving material (modified silicone) was omitted and the film thickness of the silver coating layer was set to 64 μm.

Reference Example 1

A bioelectrode was produced in the same manner as in Example 1 except that the film thickness of the silver coating layer was set to 59 μm and the salt water treatment was omitted.

Reference Example 2

A bioelectrode was produced in the same manner as in Example 2 except that the salt water treatment was omitted.

Reference Example 3

A bioelectrode was produced in the same manner as in Example 3 except that the salt water treatment was omitted.

2. Evaluation Method (1) Electrocardiogram Measurement

Figure 4:
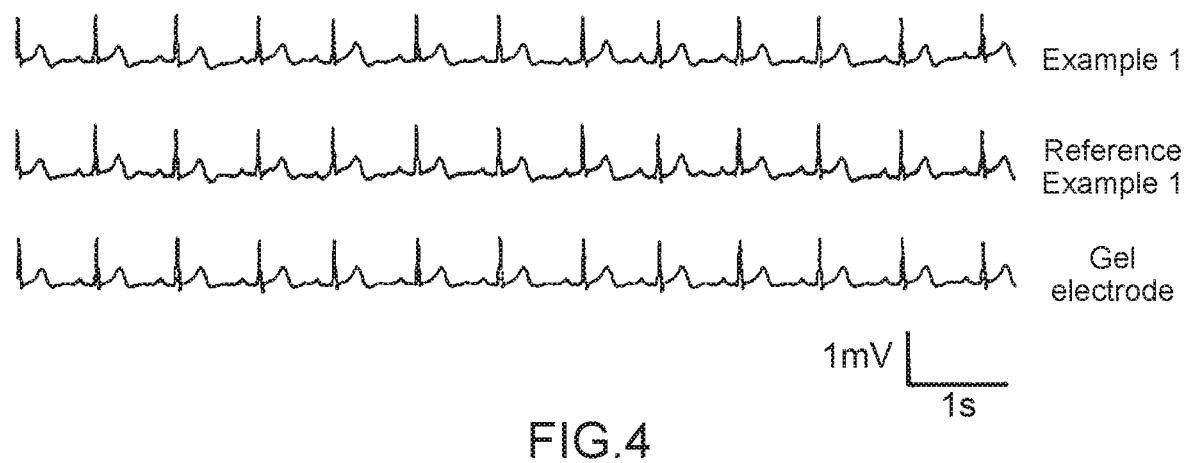
FIG. 4 is a view illustrating electrocardiogram waveforms of an adult male measured using the bioelectrode.

The bioelectrodes (sheets) obtained in Example 1 and Reference Example 1 were each punched to a diameter of 19 mm to produce a bioelectrode for electrocardiogram measurement, and a circuit to be connected to a human body and an electrocardiogram measuring apparatus was formed. Thereafter, an electrocardiogram of an adult male was measured, and waveforms displayed in the electrocardiograph were recorded. Additionally, as a reference, a commercially available gel electrode (wet electrode) was used to record electrocardiogram waveforms in the same manner. The results are shown in FIG. 4.

(2) Surface Resistance

The silver coating layer surface of each bioelectrode (before the bending test mentioned below) obtained in Examples 1 to 3, Comparative Examples 1 and 2, and Reference Examples 1 to 3 was measured for the surface resistance using a low resistivity meter "Loresta" manufactured by Mitsubishi Chemical Analytech Co., Ltd. (using a PSP terminal) by a four-terminal method. The results are shown in Table 1.

(3) Strain Resistance

Figure 5:
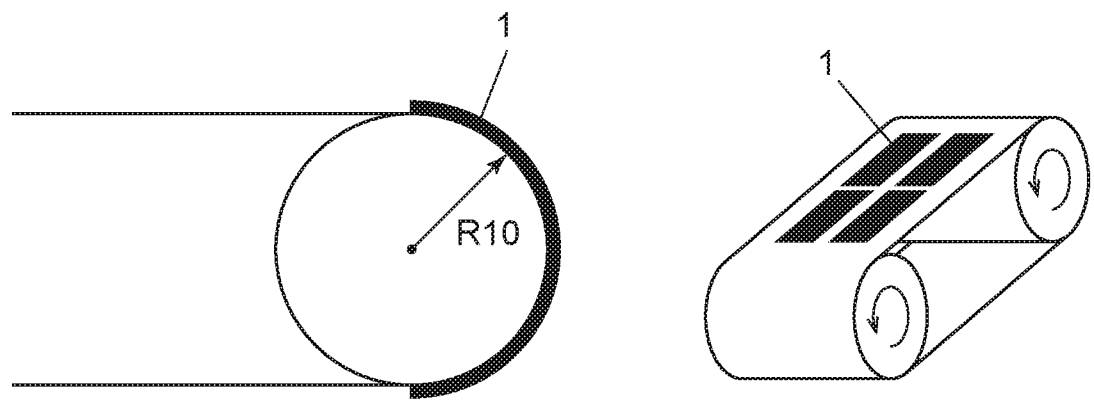
FIG. 5 is a conceptual view of a conveyor belt used in a bending test.
Figure 6:
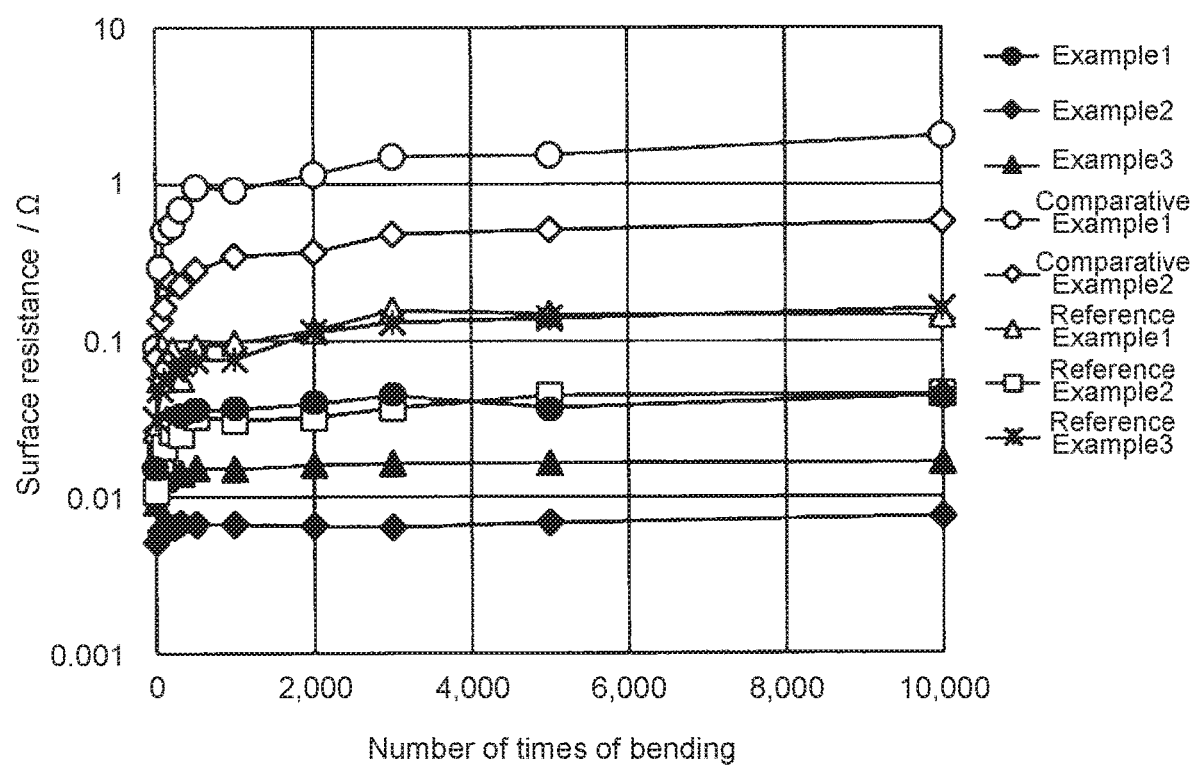
FIG. 6 is a view illustrating dependency of the surface resistance on the number of times of bending.

The bioelectrodes obtained in Examples 1 to 3, Comparative Examples 1 and 2, and Reference Examples 1 to 3 were each punched to a size of 20 mm×60 mm. A bending test was conducted in which the surface of the conductive rubber electrode of each bioelectrode was attached onto a conveyor belt illustrated in FIG. 5 and rotated to repetitively apply deformation (external force). Here, each bioelectrode was bent at a radius of 10 mm, and a total of 10000 times of bending was conducted in 5000 seconds (2 times/second). The surface resistance was measured every prescribed number of times in the same manner as in the above-described "(2) Surface Resistance". The results are shown in FIG. 6. Additionally, the measurement results of the change rate of the surface resistance after 10000 times of bending based on the initial surface resistance are shown in Table 1.

3. Evaluation

It can be seen from FIG. 4 that the bioelectrodes of Example 1 and Reference Example 1 each can measure an electrocardiogram comparable to that of a commercially available gel electrode (wet electrode) and satisfactorily function as a bioelectrode.

From Table 1, it can be seen that, in the bioelectrode of Example 1, the surface resistance has decreased and the electrical conductivity has increased in comparison with those of Comparative Examples 1 and 2 and Reference Examples 1 to 3.

From Table 1 and FIG. 6, when the bending test was conducted 10000 times, the absolute value of the surface resistance of Example 1 was one-thirds to one-fiftieth of that of Comparative Examples 1 and 2 and Reference Examples 1 to 3. Also as for the change rate in the surface resistance, the change rate of Example 1 is 2.85 times, and it can be seen that the strain resistance is enhanced.

Also as for Examples 2 and 3, an excellent effect was confirmed as in Example 1.

What is claimed is:

1. A bioelectrode comprising:

a conductive rubber electrode; and a silver coating layer provided on the conductive rubber electrode and containing a silicone rubber and silver particles, wherein the silver coating layer contains a modified silicone and contains ions for ion conduction among the silver particles, and the modified silicone contains at least one selected from the group consisting of polyglycerin-modified silicones, and polyglycerin-alkyl-comodified silicones.

TABLE 1

| | | | Example 1 | Example 2 | Example 3 | Comparative Example 1 | Comparative Example 2 | Reference Example 1 | Reference Example 2 | Reference Example 3 |
|---|---|---|---|---|---|---|---|---|---|---|
| Silver coating layer (amount compounded expressed in parts by weight) | Binder | KE-106 | 100 | 100 | 100 | 100 | 100 | 100 | 100 | 100 |
| | Silver particles | FA-D-3 | 150 | 150 | 150 | 150 | 150 | 150 | 150 | 150 |
| | | G-35 | 150 | 150 | 150 | 150 | 150 | 150 | 150 | 150 |
| | Modified silicone | KF-6015 (Polyether-modified silicone) | 10 | 20 | — | — | — | 10 | 20 | — |
| | | KF-6106 (Polyglycerin-modified silicone) | 10 | — | 20 | — | — | 10 | — | 20 |
| Evaluation | Salt water treatment | | Yes | Yes | Yes | No | Yes | No | No | No |
| | Surface resistance [Ω] | | 0.0145 | 0.00560 | 0.0100 | 0.0479 | 0.0328 | 0.0180 | 0.00953 | 0.0226 |
| | Strain resistance (bending test) | Initial surface resistance [Ω] | 0.0154 | 0.00519 | 0.00919 | 0.0916 | 0.0775 | 0.0269 | 0.0109 | 0.0310 |
| | | Surface resistance after 10000 times of bending [Ω] | 0.0439 | 0.00757 | 0.0166 | 2.03 | 0.581 | 0.146 | 0.0453 | 0.160 |
| | | Change rate [times] | 2.85 | 1.46 | 1.80 | 22.2 | 7.50 | 5.43 | 4.16 | 5.18 |

2. The bioelectrode according to claim 1, wherein the ions include ions derived from at least one selected from the group consisting of chloride salts, sulfates, and carbonates.

\* \* \* \* \*